(12) United States Patent
Tero

(10) Patent No.: US 8,333,200 B2
(45) Date of Patent: Dec. 18, 2012

(54) NASAL INTERFACE DEVICE

(76) Inventor: Robert Tero, Bayonne, NJ (US)

( * ) Notice: Subject to any disclaimer, the term of this patent is extended or adjusted under 35 U.S.C. 154(b) by 0 days.

(21) Appl. No.: 13/147,201

(22) PCT Filed: Feb. 4, 2010

(86) PCT No.: PCT/US2010/023159
§ 371 (c)(1),
(2), (4) Date: Jul. 31, 2011

(87) PCT Pub. No.: WO2010/091157
PCT Pub. Date: Aug. 12, 2010

(65) Prior Publication Data
US 2011/0284001 A1    Nov. 24, 2011

Related U.S. Application Data

(60) Provisional application No. 61/149,807, filed on Feb. 4, 2009.

(51) Int. Cl.
*A61M 15/08* (2006.01)
(52) U.S. Cl. ......... 128/207.18; 128/204.18; 128/204.26; 128/205.11; 128/205.24; 128/207.16
(58) Field of Classification Search ............. 128/204.18, 128/204.26, 205.11, 205.24, 207.16
See application file for complete search history.

(56) References Cited

U.S. PATENT DOCUMENTS

| | | | |
|---|---|---|---|
| 1,125,542 A | 1/1915 | Humphries | |
| 4,854,574 A * | 8/1989 | Larson et al. | 482/13 |
| 4,989,599 A | 2/1991 | Carter | |
| 5,074,299 A | 12/1991 | Dietz | |
| 5,099,836 A * | 3/1992 | Rowland et al. | 128/204.23 |
| 5,682,881 A | 11/1997 | Winthrop | |
| 6,568,387 B2 * | 5/2003 | Davenport et al. | 128/200.24 |
| 6,668,828 B1 | 12/2003 | Figley et al. | |
| 6,926,005 B1 * | 8/2005 | Colman et al. | 128/207.14 |
| 8,001,966 B1 | 8/2011 | Goldstein et al. | |
| 2002/0100478 A1 * | 8/2002 | Prime et al. | 128/205.24 |
| 2003/0189492 A1 * | 10/2003 | Harvie | 340/573.1 |
| 2004/0045552 A1 * | 3/2004 | Curti et al. | 128/207.18 |

(Continued)

FOREIGN PATENT DOCUMENTS

| | | |
|---|---|---|
| WO | 2005014080 | 2/2005 |
| WO | 2010023590 | 3/2010 |

OTHER PUBLICATIONS

PCT/US2010/023159 International Preliminary Report on Patentability, Aug. 9, 2011.
PCT/US2010/023159 Written Opinion, Oct. 18, 2010.
PCT/US2010/023159 International Search Report, Oct. 19, 2010.

(Continued)

*Primary Examiner* — Clinton T Ostrup
(74) *Attorney, Agent, or Firm* — Joseph E. Maenner; Maenner & Associates, LLC

(57) ABSTRACT

A nasal interface device delivers a high flow rate of a gas having a pressure that is adjustable to a patient. The device includes a nasal insert that is adapted to deliver pressurized gas to a nasal cavity of the patient, and receive and direct expired air. The nasal insert has a pressurized breathing gas delivery port and an expired gas port. An expiratory limb pressure regulator is in fluid communication with the expired gas port.

20 Claims, 8 Drawing Sheets

U.S. PATENT DOCUMENTS

| | | | |
|---|---|---|---|
| 2004/0244804 A1 | 12/2004 | Olsen et al. | |
| 2005/0121033 A1* | 6/2005 | Starr et al. | 128/204.18 |
| 2006/0005842 A1* | 1/2006 | Rashad et al. | 128/207.18 |
| 2006/0266361 A1 | 11/2006 | Hernandez | |
| 2007/0107737 A1* | 5/2007 | Landis et al. | 128/207.18 |
| 2007/0125380 A1 | 6/2007 | Acker et al. | |
| 2010/0113956 A1 | 5/2010 | Curti et al. | |

OTHER PUBLICATIONS

PCT application PCT/US2012/035713 "Invitation to Pay Additional Fee and, Where Applicable, Protest Fee" and "Communication Relating to the Results of the Partial International Search", mailed Jul. 17, 2012.

* cited by examiner

NASAL INTERFACE DEVICE

CROSS-REFERENCE TO RELATED INVENTION

The present application claims the benefit of PCT application Serial No. PCT/US2010/23159, filed on Feb. 4, 2010, which claims the benefit of U.S. Provisional Patent Application Ser. No. 61/149,807, filed Feb. 4, 2009, which are both incorporated by reference in their entireties.

FIELD OF THE INVENTION

The present invention relates to a nasal interface device that functions to deliver high flow and has the ability to deliver pressurized breathing gas to a patient.

BACKGROUND OF THE INVENTION

Current respiratory ventilation systems to treat mild to moderate respiratory failure in humans, commonly of hypoxemic origin, include nasal Continuous Positive Airway Pressure (nCPAP) and humidified high flow therapy. nCPAP is the most widely used system because it can be administered non-invasively and can effectively increase patients functional residual capacity (FRC), allowing for air sacs to open and resulting in improved oxygenation. Diseases that can be treated with such a system include mild to moderate infant respiratory distress syndrome, atelectasis, pneumonia, pulmonary edema, congestive heart failure and many others in patients ranging from premature babies to adults. The nCPAP system, however, presents many problems, including the labor intensiveness of applying the head gear to the patient, and the bulky and cumbersome head gear that can lead to stress, claustrophobia and discomfort to patients. Physical conditions such as nasal irritation, pressure sores and skin breakdown are also a common complication.

The humidified high flow therapy system has the advantage of improved comfort as well as reduced risk of skin breakdown because of the smaller size of the head gear (i.e., nasal cannula). However, the humidified high flow therapy presents problems with uncontrolled pressurized environment, the risk of pressure build-up in the patient's respiratory cavity, and the inability of this therapy to control and set a CPAP. As a result of the known problems, clinicians are reluctant to apply this system due to the unregulated airway pressure (i.e., CPAP).

There exists a need to provide a small, lightweight and non-intrusive headgear with the ability to regulate pressure in the patient's respiratory cavity.

SUMMARY OF THE INVENTION

Devices in accordance with the instant invention overcome the problems of the prior art. The user of the devices in accordance with the present invention is also provided with the ability to customize the nasal interface device according to the user's needs. Additionally, embodiments of the instant invention are adaptable such that they can be integrated with different respiratory ventilation systems. Furthermore, because the devices may be customized to the size of the patient's facial features, the typical bulkiness and irritation of current respiratory ventilation systems that are capable of controlling CPAP are overcome.

By applying one or more embodiments of the instant invention, patients can comfortably receive gas at a desired flow rate and clinicians can measure and easily adjust the CPAP.

The advantages of the nasal interface device of the present invention include (a) its simplicity and small size, allowing the device to be easily applied with minimal treatment-patient interruption (i.e., it does not require the use of bulky headgear, nasal mask or head straps and thus reduces stress to the patient); (b) the ability to provide high flow and nCPAP; (c) the ability of the clinician to administer, regulate, and monitor nCPAP with little effort; (d) the adaptability and versatility of the device to be interfaced with most, if not all, respiratory ventilation systems and humidified high flow systems that are well-known to a skilled artisan; (e) the ability of the device to convert high flow systems, including but not limited to VAPOTHERM®, Fisher and Paykel MR 850 systems, into a CPAP system; and (f) cost effectiveness because the device does not require many parts.

In accordance with one or more aspects of the present invention, a nasal interface device for delivering high flow and continuous positive airway pressure in a controlled and regulated manner to a patient is configured so that a clinician can quickly and easily apply the device to a patient, measure the CPAP and adjust the nCPAP accordingly. The nasal interface device is further configured so that a clinician can easily integrate the nasal interface device to existing respiratory ventilation systems and humidified high flow systems that are well-known to a skilled artisan.

In an exemplary embodiment, the nasal interface device comprises a nasal insert having a cavity in which a bidirectional tee flow deflector is situated, nasal prongs, and various tubing attachments. The nasal insert is configured to receive breathing gas, the gas generated from any generator well-known to a skilled artisan, through an injector tubing that enters the nasal insert through the bidirectional tee flow deflector. The breathing gas coming from the bidirectional tee flow deflector is directed towards and delivered in equal amounts through two nasal prongs into the nasal cavity of the patient. As the patient expires air through the nose into the nasal prongs, the expired air, along with any excess breathing gas, is directed by the bidirectional tee flow deflector through the nasal insert and into a series of expiratory tubes. This mixture of expired air and excess breathing gas travels through the expiratory tubes to the expiratory limb tubing and out to the environment through expiratory limb pressure regulator. The flow of air and gas out of the expiratory limb pressure regulator can be adjusted so that the pressure in the nasal interface can be maintained.

Additionally the nasal insert may further be attached to pressure tubing connected to a pressure measuring device, such as a manometer, and expiratory limb tubing connected to an expiratory limb pressure regulator. The clinician can measure the gas pressure in the nasal insert by the manometer and adjust the expiratory limb pressure regulator accordingly to increase or decrease the CPAP.

The nasal interface device is a closed system that creates a pressurized environment, whereby breathing gas is forced through the injector tubing, the bidirectional tee flow deflector of the nasal insert and exits the nasal prongs and/or the expiratory limb pressure regulator. The pressurized environment allows the breathing gas flow and the pressure (i.e., CPAP) to be monitored and controlled. The pressure can be monitored by attaching a manometer to the optional pressure tubing coming from the nasal insert.

Application of the nasal interface device on a patient can be customized to suit the age and size of the patient. Generally, the nasal prongs are placed near or in a patient's nostrils such that the nasal insert is resting just outside of the patient's nose. The nasal prongs may be narrow to fit a premature baby or wide to fit an adult. The nasal prongs may be straight or curved depending on whether the prongs are to be placed just outside the nasal cavity (i.e., in premature babies and neonates), or further inside the nasal cavity (i.e., in infants, children and adults). Within each age group, the thickness of the nasal prongs may be also adapted to affect the high flow rate of the breathing gas flow and/or the air pressure. The injector tubing and expiratory tubes, and optionally the pressure tubing, may be placed around the patient's head to aid in securing the nasal insert in place. The expiratory tubes may be flexible so as to allow a variety of configurations about the head. Optionally the expiratory tubes may be rigid and contoured so that they may be placed over the ears of the patient.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILED DESCRIPTION OF EMBODIMENTS OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

Figure 1:
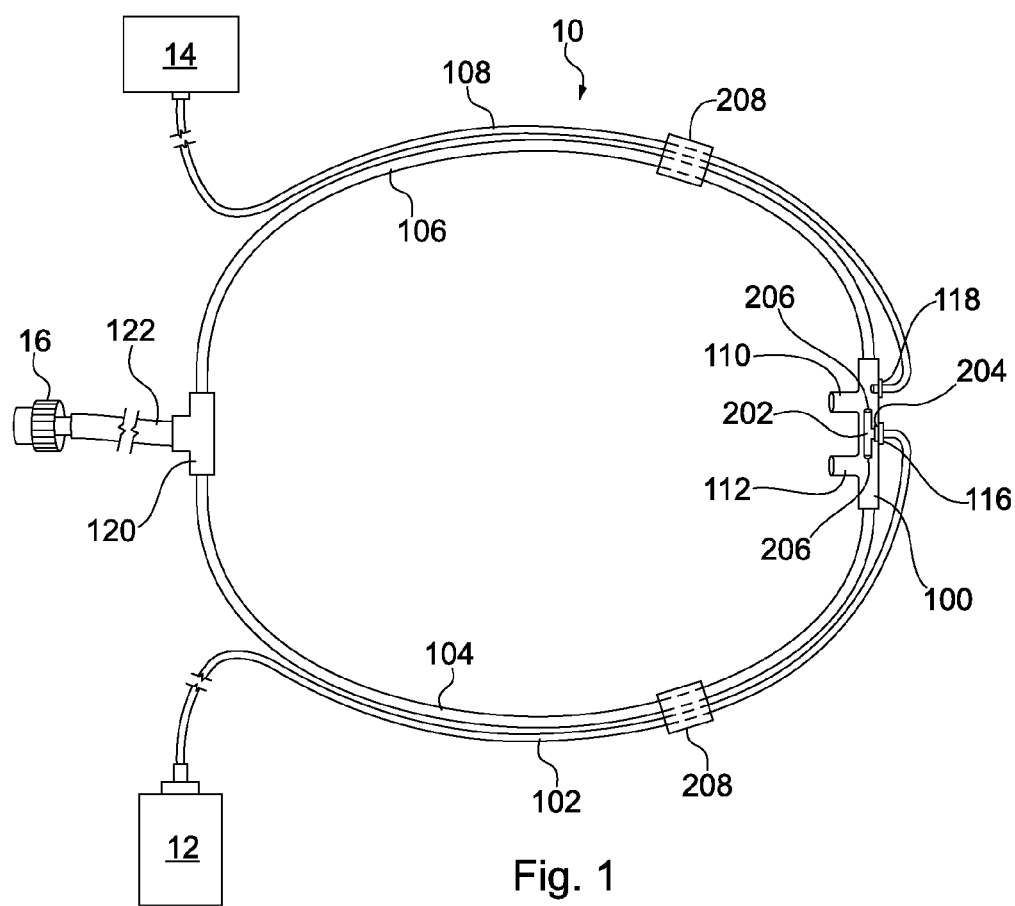
FIG. 1 depicts a respiratory ventilation system employing a nasal interface device, having a bidirectional tee flow deflector in the nasal insert, integrated with a breathing gas continuous positive airway pressure (CPAP) generator, a pressure measuring device and an expiratory limb pressure regulator in accordance with one embodiment of the present invention.

Turning now to the details of the drawings, FIG. 1 is a view of a nasal interface device 10, embodying one or more aspects of the present invention, that is integrated with a respiratory ventilation system. The nasal interface device 10 delivers a high flow rate of a gas having a pressure that is adjustable to a patient and includes a nasal insert 100 having a hollowed cavity in which a bidirectional tee flow deflector 202 is situated. The nasal insert 100 is adapted to deliver pressurized gas to a nasal cavity of the patient, and to receive and direct expired air. The nasal insert 100 also includes nasal prongs 110 and 112 and four openings that are connected to a series of tubing including an injector tubing 102 via a pressurized gas delivery port 116, a pressure tubing 108 via an outlet port 118, and expiratory conduits or tubes 104 and 106. It is contemplated that the pressurized gas delivery port 116 and outlet port 118 may be located at any position in the nasal insert 100. The expiratory tubes 104 and 106 are in fluid communication with a tubing connector device 120, with the tubing connector device 120 in fluid communication with an expiratory limb tubing 122 that is further connected to an expiratory limb pressure regulator 16.

The bidirectional tee flow deflector 202 includes an inlet end 204 coupled to the pressurized gas delivery port 116 and outlet ends 206. The bidirectional tee flow deflector 202 is situated in the hollow cavity of the nasal insert 100 such that the inlet end 204 is connected to the end of the injector tubing 102 and the outlet ends 206 are situated near the nasal prongs 110 and 112 such that any breathing gas flowing out of the outlet ends 206 would preferentially flow into the nasal prongs 110 and 112 upon inspiration of a patient. It is contemplated that the outlet ends 206 are shaped so as to aid in directing breathing gas exiting the outlet ends 206 towards the nasal prongs 110 and 112. It is also contemplated that the bidirectional tee flow deflector 202 is situated in the nasal insert 100 and shaped so as to aid in diverting air coming in from the nasal prongs 110 and 112, upon expiration of air by a patient, to the expiratory tubes 104 and 106. The bidirectional tee flow deflector 202 functions to direct the breathing gas flow towards the nasal prongs 110 and 112 and to evenly distribute the breathing gas between the nasal prongs 110 and 112, resulting in even air flow to both nasal cavities of the patient during inspiration. The bidirectional tee flow deflector 202 further functions to divert expired air and excess breathing gas flow to the expiratory tubing 104 and 106 during expiration. The dual function of the bidirectional tee flow deflector 202 results in breathing gas flow support during inspiration and reduced expiratory resistance, while allowing positive distending pressures and ultimately reduction of work of breathing. The bidirectional tee flow deflector 202 may be made from soft flexible material selected from any suitable biocompatible flexible material such as latex, silicone, rubber, carbon fiber, or other synthetic fiber. The bidirectional tee flow deflector 202 may also be made from rigid material selected from any suitable rigid biocompatible material such as plastic, metal, wood or any material that maintains its shape, and is resistant to breaking or snapping.

It is contemplated that the injector tubing 102 is tethered to a length of one of the expiratory tubes 104 and 106 via at least one removable connector 208 so as to reduce the risk of loose tubing being accidentally pulled or crimped. The removable connector 208 may also slide along the length of the tubing such that the loop resulting from the combined tubing and nasal insert 100 is adjustable in size, allowing the nasal interface device 10 to be tightened or loosened around the patient's head, and functions to safely hold the nasal insert 100 in place. It is also contemplated that the injector tubing 102 may be inserted inside one of the expiratory tubes 104 and 106, which functions to reduce the risk of entanglement of multiple tubing. Additionally, the injector tubing 102 and one of the expiratory tubes 104 and 106 and/or the pressure tubing 108 and one of the expiratory tubes 104 and 106 may be fused such that they form a dual or multiple lumen tubing. Heat from expired gases flowing through expiratory tube 104 may be used to heat the breathing gas in injector tubing 102, reducing the occurrence of rainout within injector tubing 102.

Breathing gas produced by a breathing gas generator 12 that is connected to the injector tubing 102 is delivered to the nasal insert 100 through the injector tubing 102. One end of the injector tubing 102 is inserted through the nasal insert 100 via a pressurized gas delivery port 116 centrally located between the nasal prongs 110 and 112 and is connected to the bidirectional tee flow deflector 202. As the breathing gas exits the injector tubing 102, the breathing gas is directed through the bidirectional tee flow deflector 202 and towards the nasal prongs 110 and 112 and into the nasal cavity of the patient.

A clinician can measure the CPAP pressure of the nasal interface device 10 by a pressure measuring device 14, for example a manometer or other device that is well-known to a skilled artisan, that is connected to the nasal interface device 10 such as by the pressure tubing 108.

CPAP is influenced by two factors—leaks that occur through the nose and mouth of the patient, and the clinician's control of the breathing gas flow adjusted to slightly exceed patient demands. These factors can be controlled by the nasal interface device 10 as depicted in FIG. 1. Leakage of gas, and thus pressure, through the nose of the patient may be controlled by varying the size and fit of the nasal prongs 110 and 112 (see FIGS. 3-5 below). CPAP is mechanically maintained using an expiratory limb pressure regulator 16 that is connected to the nasal interface device 10 by the expiratory limb tubing 122. It is contemplated that the expiratory limb pressure regulator 16 may be a positive end expiratory pressure valve (PEEP), a water seal column or other pressure regulator that is well-known by a skilled artisan. This is accomplished when breathing gas flows are introduced through the injection tubing 102 and a mixture of excess breathing gas and expired air from the patient flow to the expiratory limb pressure regulator 16. The expiratory limb pressure regulator 16 maintains the desired CPAP pressure in the nasal interface device 10 by reducing or increasing gas flow out of the nasal interface device 10 and ensures that the gas flow delivered to the patient does not exceed the desired CPAP pressure setting. For example, if a clinician measures the CPAP pressure using the manometer and then desires to increase the CPAP pressure in a nasal interface device 10 having a PEEP valve, the clinician may adjust the PEEP valve by the turning the valve to reduce the air flow out of the nasal interface device 10.

Figure 2:
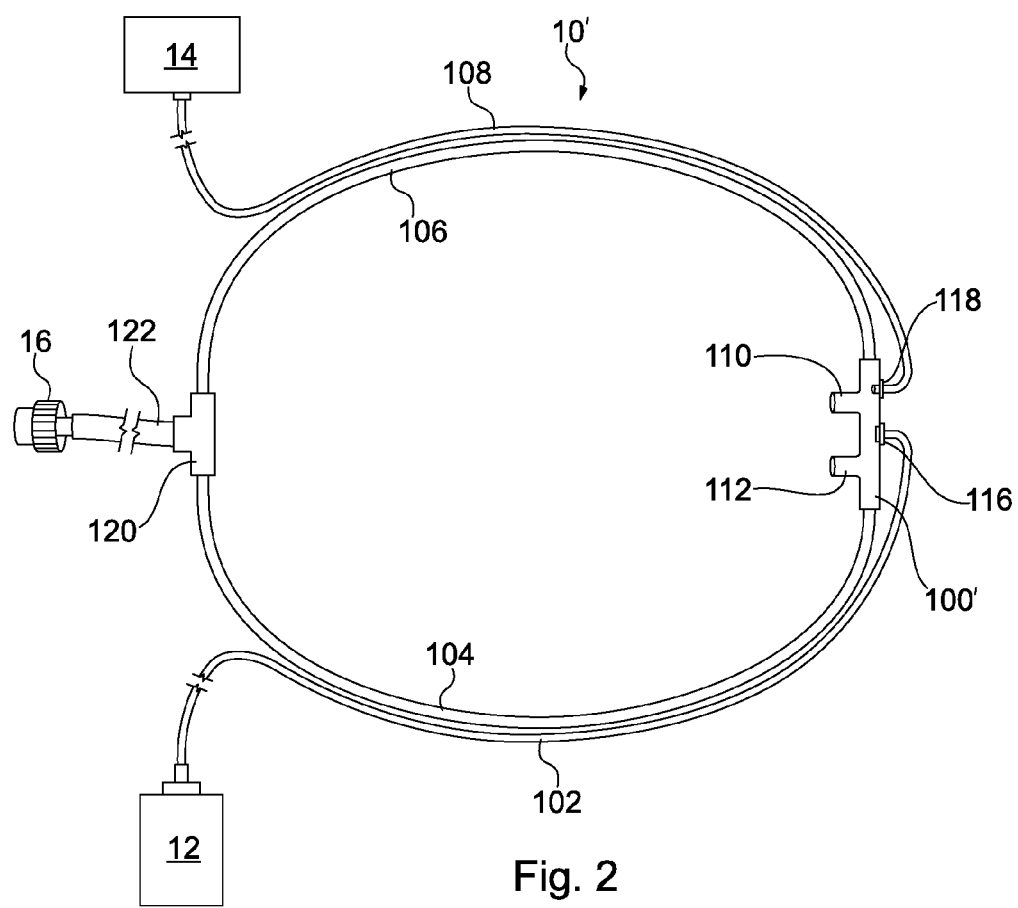
FIG. 2 depicts another embodiment of the nasal interface device of FIG. 1 without a bidirectional tee flow deflector in the nasal insert, and removable connectors to tether the injector tubing and expiratory tube or pressure tubing and expiratory tube together.

FIG. 2 is a view of the nasal interface device 10' in which the nasal insert 100' does not include the bidirectional tee flow deflector 202. One end of the injector tubing 102 is inserted through the nasal insert 100 via a pressurized gas delivery port 116 centrally located between the nasal prongs 110 and 112. As the breathing gas exits the injector tubing 102, the breathing gas flow is directed towards the nasal prongs 110 and 112 such that upon inspiration by the patient, the breathing gas is preferentially drawn through the nasal prongs 110 and 112 and into the nasal cavity of the patient.

Figure 3:
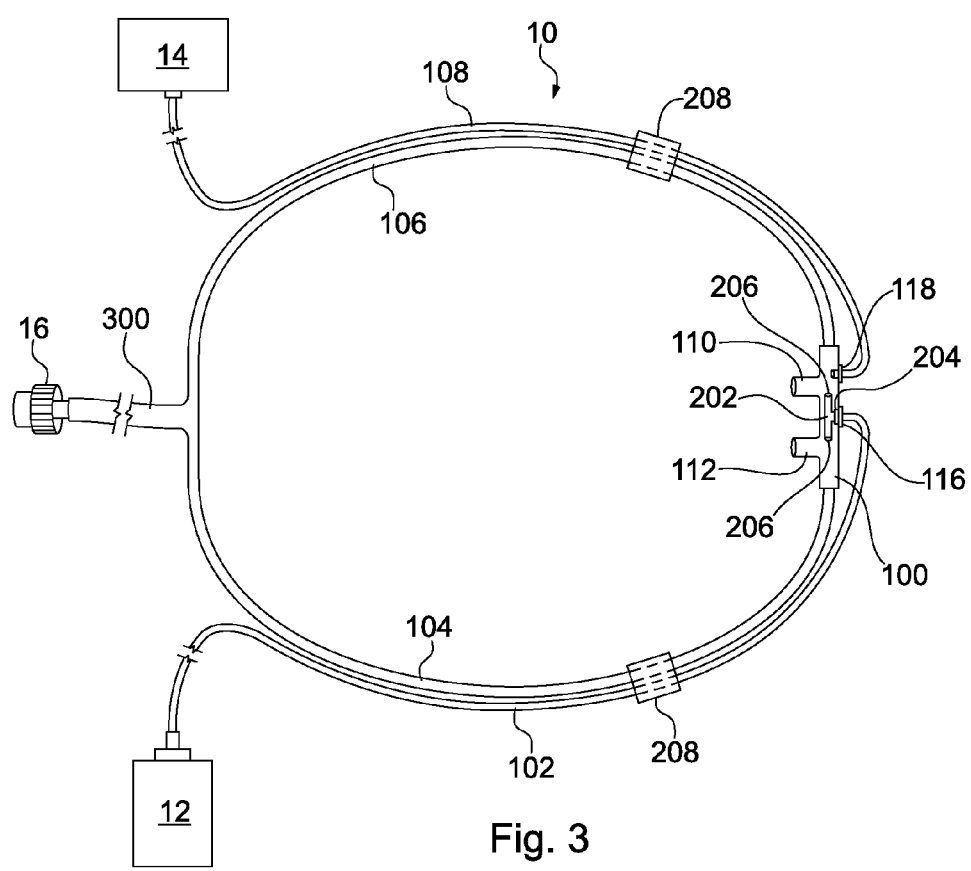
FIG. 3 depicts another embodiment of the nasal interface device of FIG. 1 in which the expiratory tubes are fused together and form a fused expiratory tube.

FIG. 3 is a view of the nasal interface device 10 in which the expiratory tubes 104 and 106 are joined together at a determined position along their lengths, without the use of the tube connector device 120, and form a fused expiratory tube 300. The fused expiratory tube 300 is further connected to an expiratory limb pressure regulator 16.

Figure 4:
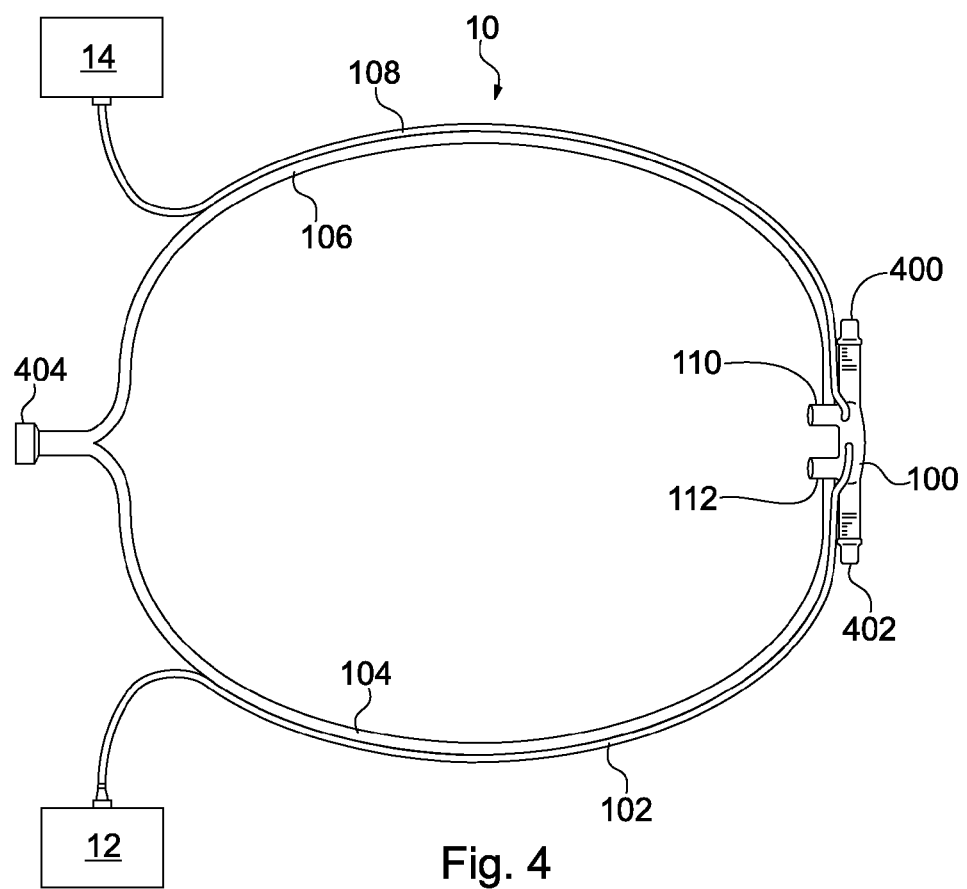
FIG. 4 depicts another embodiment of the nasal interface device of FIG. 3 having expiratory pressure regulators connected directly to the nasal insert.

FIG. 4 is a view of the nasal interface device 10 in which pressure regulators 400 and 402 are integral with the nasal insert 100. The pressure regulators 400 and 402 may be a positive end expiratory pressure valve (PEEP), or other pressure regulator that is well-known by a skilled artisan. The pressure regulators are adjustable and function to regulate the air pressure (CPAP).

Although not shown, it is contemplated that the nasal insert 100 is fused to a single pressure regulator. The expiratory limb tubing 122 is connected to an end cap 404. The end cap 404 prevents any gas from escaping from the expiratory tubes 104 and 106 so that air pressure can be maintained. It is also contemplated that the expiratory tubes 104 and 106 may be solid tubing, such that the expiratory tubes 104 and 106 would not fill with air and would function to aid in keeping the nasal interface device 10 situated on the patient and not affect the air pressure.

Figure 5A:
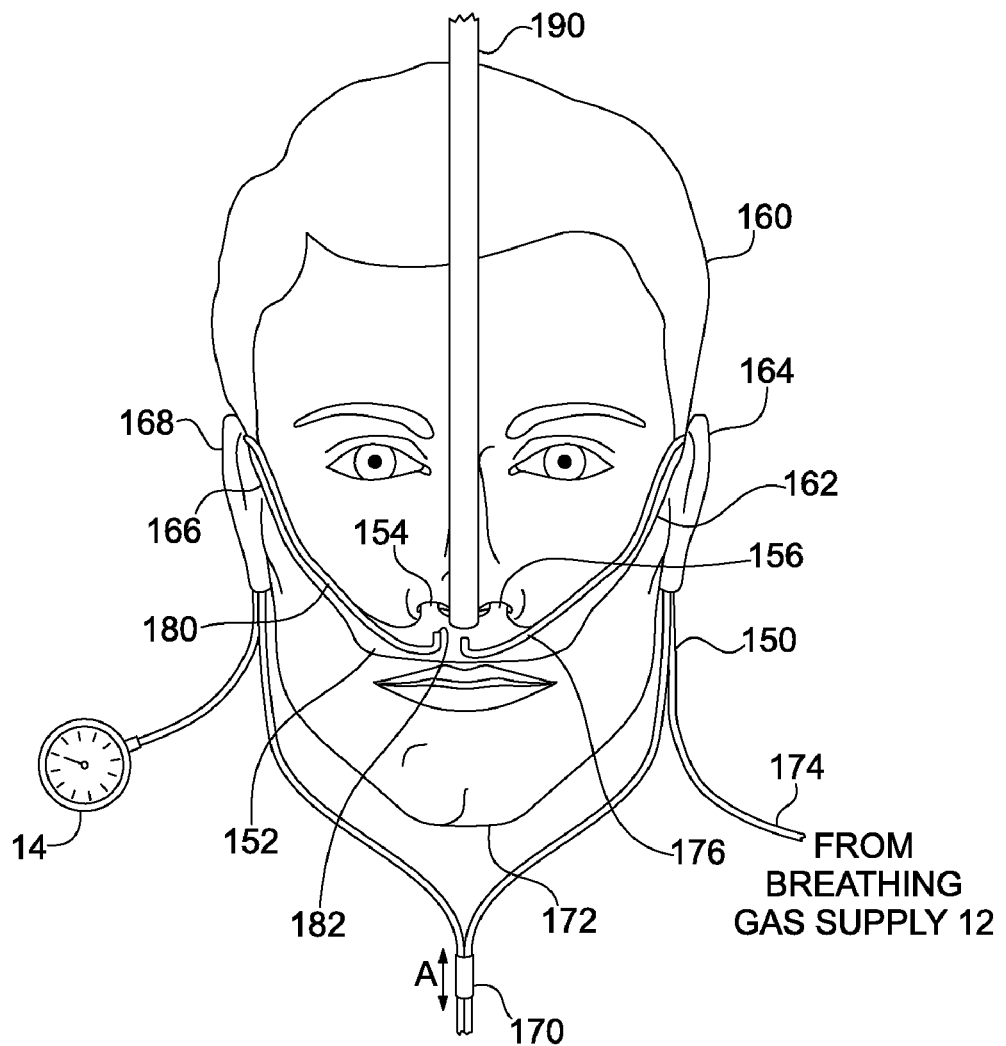
FIG. 5A depicts a front elevational view of another exemplary embodiment of a nasal interface device according to the present invention being used on a patient.
Figure 5B:
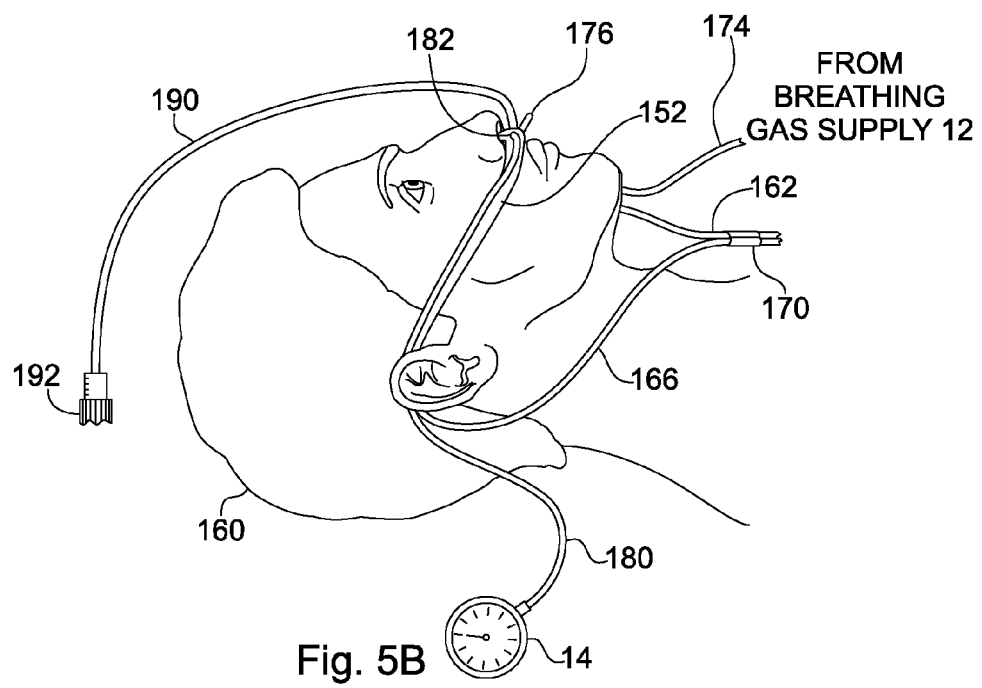
FIG. 5B depicts a side view of the nasal interface device of FIG. 5A being used in an exemplary fashion on the patient.

In an alternative exemplary embodiment of the present invention, illustrated in FIGS. 5A and 5B, a nasal interface device 150 includes a nasal insert 152 having nasal prongs 154, 156 that are insertable into the nares of a patient 160. Nasal insert 152 includes a first end portion 162 that extends from a side of nasal insert 152 and may be draped over the left ear 164 of the patient 160. First end portion 162 may then extend downward to the front of patient 160. Similarly, a second end portion 166 of nasal insert 152 extends from an opposing side of nasal insert 152 and may be draped over the right ear 168 of the patient 160. Second end portion 166 may then extend downward to the front of patient 160, where first and second end portions 162, 166 may be joined to each other by a slide collar 170. Slide collar 170 is adjustable along the length of first and second end portions 162, 166, as indicated by arrow "A", to secure nasal insert 152 under the patient's chin 172, as desired.

Nasal interface device 150 also includes a breathing gas supply conduit 174 that may be coupled to breathing gas supply 12 to provide breathing gas to nasal insert 152 and prongs 154, 156 for inhalation by the patient 160. Breathing gas supply conduit 174 extends along a length of first end portion 162 of the nasal insert 152, over the left ear 164 of the patient 160, and into nasal insert 152 at interface 176. Nasal insert 152 may include a tee flow deflector 202, illustrated in FIG. 1, or may omit the tee flow deflector, as illustrated in FIG. 2.

Pressure tubing 180 extends from nasal insert 152 via an outlet port 182. Pressure tubing 180 may extend along second end portion 166 of the nasal insert 152, over the patient's right ear 168, and to manometer 14, which measures the expiration pressure of the patient 160.

An exhaust conduit 190 extends from nasal insert 152 to exhaust expired air as well as non-inhaled breathing gas from inside nasal insert 152. A pressure regulator 192 is located at an end of exhaust conduit 190. Similar to pressure regulator 16 shown in FIGS. 1-3, pressure regulator 192 maintains the desired CPAP pressure in the nasal interface device 150 by reducing or increasing gas flow out of the nasal interface device 150 and ensures that the gas flow delivered to the patient does not exceed the desired CPAP pressure setting.

Figure 6:
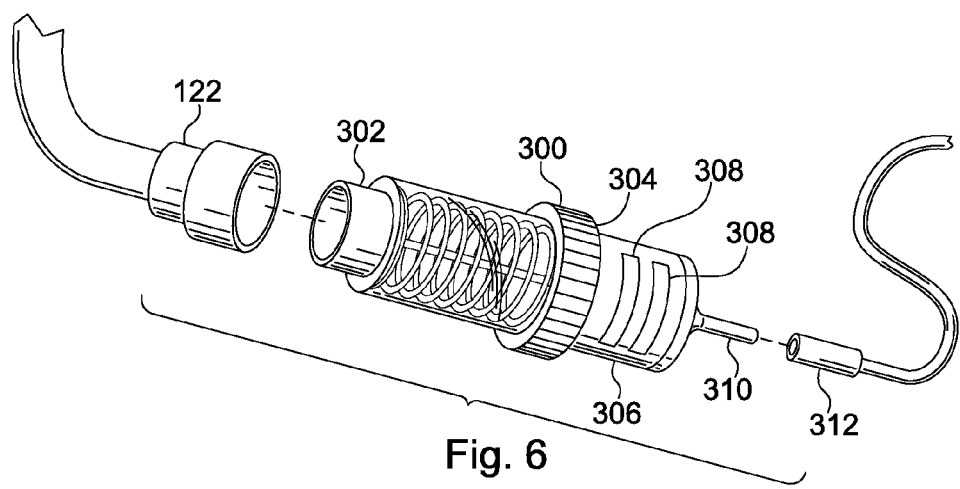
FIG. 6 depicts an exemplary embodiment of a positive end expiratory pressure valve (PEEP) pressure regulator for use with the nasal interface of the present invention.

A pressure regulator or PEEP valve according to an exemplary embodiment of the present invention is illustrated in FIG. 6. A known PEEP valve 300, such as, for example, a THRESHOLD® PEP valve, manufactured by Respironics of Murrysville, Pa., may be used. PEEP valve 300 includes an inlet 302 that is coupled to a discharge end of expiratory limb tubing 122 in place of expiratory limb pressure regulator 16 shown in FIGS. 1-3. An outlet 304 of PEEP valve 300 is coupled to a reservoir 306. Reservoir 306 includes at least one and, optionally, a plurality of, openings 308 therein to provide for fluid communication between the interior of reservoir 306 and atmosphere. A discharge end 310 of reservoir 306 is coupled to a suction tube 312. Suction tube 312 is coupled to a wall suction regulator/vacuum (not shown), which draws a vacuum on the interior of reservoir 306.

Openings 308 provide for airflow into reservoir 306 to allow minimal setting of vacuum yet still allow good amount of suction flow. If openings 308 are omitted, vacuum will affect the setting of PEEP valve 300 due to PEEP valve 300 becoming a closed system. Vacuum will thus pull vacuum directly from PEEP valve 300. Openings 308 further act as a safety mechanism in the event of inadvertent change in the vacuum or suction regulator and also allow for wide adjustment of the vacuum being drawn on PEEP valve 300. Further, a plurality of openings 308 act as a redundant feature in case of blockage of less than all openings 308.

PEEP valve 300 is used to remove excess moisture from the humidified expired gas that can collect in PEEP valve 300, which may possibly affect the function of PEEP valve 300 over time. With the vacuum on PEEP valve 300, PEEP valve 300 can be used with humidified breathing gas, which allows for long term use, as dry gas can cause discomfort to an adult patient and harm to an infant in long term applications. The use of PEEP valve 300 will allow clinicians to convert dry to a humidified application. For example, a dry application such as in an ambulance or labor and delivery can be initiated for a short term on the patient and when the patient is moved to the emergency department and/or neonatal intensive care unit, clinicians can convert to a humidified application with simply adding PEEP valve 300 for long term use without changing devices.

Figure 7:
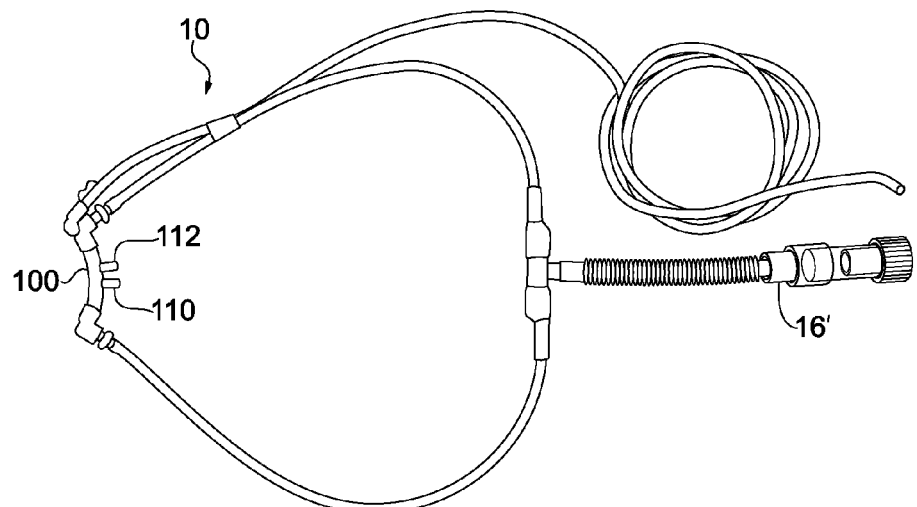
FIG. 7 depicts a nasal interface device having a nasal insert and nasal prongs suited for premature babies and neonates, and an expiratory limb tubing connected to a positive end expiratory pressure valve (PEEP) pressure regulator.
Figure 8:
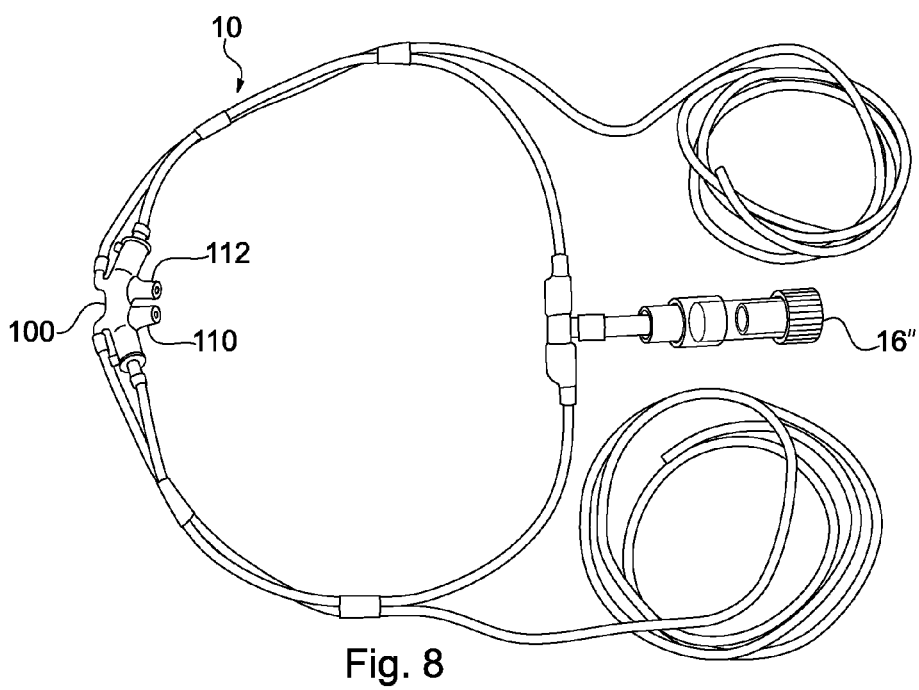
FIG. 8 depicts a nasal interface device having a nasal insert and nasal prongs suited for infants and adults, and an expiratory limb tubing connected to a positive end expiratory pressure valve (PEEP) pressure regulator.

FIGS. 7 and 8 show the nasal interface device 10 having variously sized nasal inserts 100 and expiratory limb pressure regulators 16. It is contemplated that the nasal insert 100 and nasal prongs 110 and 112 would vary in size and diameter depending upon the age and size of the patient, and also upon the desire to increase or decrease the high flow gas rate and air pressure. For example, FIG. 7 depicts the nasal interface device 10 showing the nasal insert 100 and nasal prongs 110 and 112 reduced in size suitable for premature babies and neonates, and a water seal column pressure regulator 16'. FIG. 8 depicts the nasal interface device 10 showing the nasal insert 100 and nasal prongs 110 and 112 customized to a size suitable for infants to adults, and a PEEP valve pressure regulator 16". It is also contemplated that the nasal prongs 110 and 112 may vary in shape such that they could take that shape of a straight shaft, curved, or anatomically shaped.

Nasal prongs 110 and 112 may be detachable from nasal insert 100. Nasal prongs 110 and 112 may be provided in a variety of shapes and/or sizes for selection based on the particular patient. For example, a child may require smaller nasal prongs than an adult in order to achieve the same level of sealing of the nasal prongs with the patient's nares. Alternatively, depending on the patient's physical condition, different sized nasal prongs may be required for different treatment regimens. For example, relatively loosely fitting nasal prongs may be desired to provide a deliberate leak between the nasal prongs and the patient's nares to improve $CO_2$ removal. Alternatively, a relatively tight seal between the nasal prongs and the patient's nares may be desired to obtain consistent air pressure for improved oxygenation to the patient.

Figure 9:
FIG. 9 depicts a nasal interface device having expiratory tubes being used by a neonate.
Figure 10:
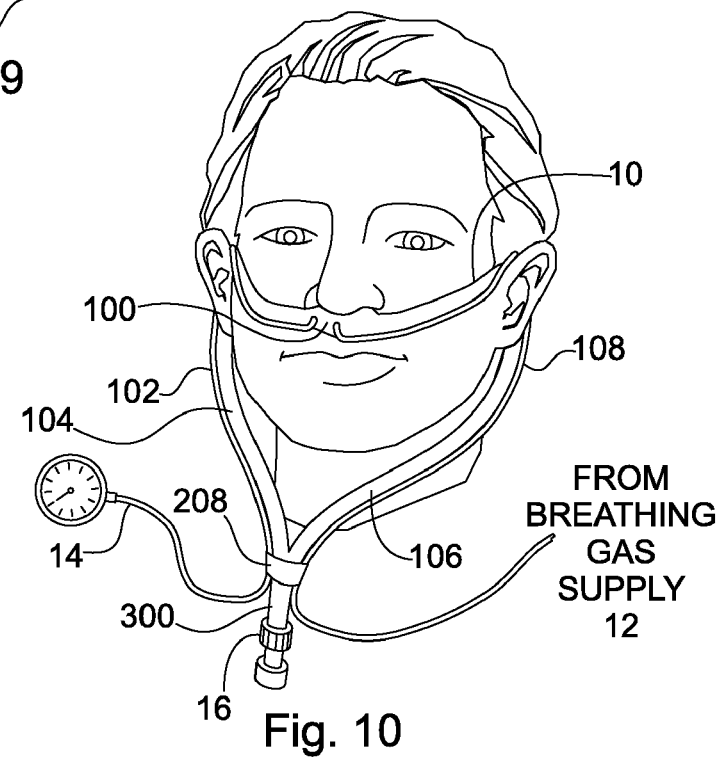
FIG. 10 depicts a nasal interface device having expiratory tubes contoured to fit over the ears being used by an adult.

FIGS. 9 and 10 depict the nasal interface device 10 being used by patients of varying age. It is contemplated that the expiratory tubes 104 and 106 may be flexible and/or corrugated so that the tubes may be contoured around a patient's head and shoulders. FIG. 9 shows a premature baby or neonate patient with a nasal interface device 10 having flexible expiratory tubes 104 and 106 that are easily contoured to wrap around the baby's head. It is also contemplated the expiratory tubes 104 and 106 may be rigid such that they are contoured a patient's head, for example, to wrap over the ears of a patient. FIG. 10 shows an adult patient with a nasal interface device 10 having rigid expiratory tubes 104 and 106 that are contoured to fit around the ears. The removable connector 208 is shown to tether the fused expiratory tube 300 and the injector tubing 102 and pressure tubing 108. The removable connector 208 may slide up or down, and as the removable connector 208 slides up (i.e., towards the patient's head) to a position that would tether together the expiratory tubes 104 and 106, injector tubing 102 and pressure tubing 108, a loop resulting by the combined tubing and nasal insert 100 will become reduced in size and functions to safely hold the nasal interface device 10 in place. To remove the nasal interface device 10 from the patient, the removable connector 208 can be easily slid down (i.e., away from the patient's head) along the tubing to increase the loop so that the nasal interface device 10 can be lifted away from around the patient's head.

Additionally, both the length and inner diameter of the injector tubing 102, expiratory tubes 104 and 106 and pressure tubing 108 may vary to allow for different gas flow, pressures, and reduction of excess humidification (i.e., moisture buid-up). Variations and relative differences in length and inner diameter will allow a clinician to set the desired pressure to be produced within the nasal interface device 10 and would allow for a range of flowrates, for example low to very low flowrates.

Although exemplary embodiments of the invention have been disclosed for an illustrative purpose, those skilled in the art would appreciate that many additions, modifications, and substitutions are possible without departing from the scope and spirit of the invention.

The invention claimed is:

1. A nasal interface device for delivering a high flow rate of a breathing gas having a controlled pressure, the device comprising:
   a nasal insert adapted to deliver pressurized breathing gas to a nasal cavity of the patient, and to receive and direct expired air, the nasal insert having a pressurized breathing gas delivery port and an expired gas port, wherein the nasal insert comprises first and second nasal prongs extending along a first side of the nasal insert and wherein the pressurized breathing gas delivery port extends along a second side of the nasal insert, opposed from the first side of the nasal insert, the pressurized breathing gas delivery port connected to a pressurized breathing gas supply; and
   an expiratory limb pressure regulator in fluid communication with the expired gas port.

2. The nasal interface device according to claim 1, wherein the nasal insert further comprises a bidirectional flow deflector coupled to the pressurized breathing gas delivery port and adapted to evenly distribute pressurized breathing gas to each of two nasal prongs in fluid communication with the pressurized breathing gas delivery port and to direct expired air toward the expired gas port.

3. The nasal interface device according to claim 1, further comprising a pressurized breathing gas supply tube coupled to the pressurized breathing gas delivery port and an expiratory gas line coupled to the expired gas port.

4. The nasal interface device according to claim 3, wherein the expiratory gas line is adjacent to and in engagement with the pressurized breathing gas supply tube.

5. The nasal interface device according to claim 4, wherein the expiratory limb pressure regulator comprises:
- a regulator outlet;
- a reservoir coupled to the regulator outlet, the reservoir having at least one opening extending therethrough; and
- a reservoir outlet adapted to be coupled to suction tubing.

6. The nasal interface device according to claim 1, wherein the expiratory limb pressure regulator is integral with the nasal insert.

7. The nasal interface device according to claim 1, wherein the expired gas port comprises a first expired gas port and a second expired gas port.

8. The nasal interface device according to claim 7, further comprising an expired gas conduit fluidly coupling each of the first expired gas port and a second expired gas port to the expiratory limb pressure regulator.

9. The nasal interface device according to claim 1, wherein the expiratory exhaust port is disposed proximate to the pressurized breathing gas delivery port.

10. The nasal interface device according to claim 1, further comprising a pressure measuring device in fluid communication with the expired gas port.

11. A nasal insert comprising:
- an outer portion having:
  - a hollowed cavity;
  - first and second expiratory gas in fluid communication with the hollowed cavity; and
  - a pair of nasal prongs in fluid communication with the hollowed cavity, the pair of nasal prongs extending perpendicular to the expiratory gas conduits; and
- a pressurized breathing gas supply conduit extending through the outer portion such that the pressurized breathing gas supply conduit is in fluid communication with the hollowed cavity and a pressurized breathing gas supply; and
- a PEEP valve connected to the first and second expiratory gas conduits.

12. The nasal insert according to claim 11, wherein the at least one nasal prong comprises first and second nasal prongs and wherein the breathing gas supply conduit comprises a flow deflector, wherein the pressurized breathing gas connection is located at a stem of the flow deflector and wherein the pressurized breathing gas outlet comprises a first outlet end disposed proximate to the first nasal prong and a second outlet end disposed proximate to the second nasal prong.

13. The nasal insert according to claim 11, further comprising a pressure regulator directly coupled to the outer portion and in fluid communication with the hollowed cavity.

14. A nasal interface device for delivering a high flow rate of a breathing gas having a pressure that is adjustable to a patient, the device comprising:
- a nasal insert having:
  - a body forming a hollowed cavity;
  - a breathing gas inlet;
  - a pair of expiratory gas outlets extending co-linearly along the body with one outlet on each side of the body; and
  - a pair of nasal prongs extending perpendicularly from the body with respect to the expiratory gas outlets; and
- a breathing gas supply tube having a first end coupled to the breathing gas inlet;
- a pair of expiratory conduits, each of the expiratory conduits having a first end coupled to one of the expiratory gas outlets and a second end coupled to the second end of the other expiratory conduit at an expiratory tee; and
- a PEEP valve coupled to the expiratory tee.

15. The nasal interface device according to claim 14, further comprising a pressure measuring tubing providing fluid communication between the pressure measurement device and the pressure measuring connection, the pressure measuring tubing extending alongside one of the expiratory conduits.

16. The nasal interface device according to claim 15, wherein the breathing gas supply tube extends along the other of the expiratory conduits.

17. The nasal interface device according to claim 16, wherein the breathing gas supply tube is fused to the other of the expiratory conduits.

18. The nasal interface device according to claim 14, wherein the pressure measuring tubing is fused to the one of the expiratory conduits.

19. The nasal interface device according to claim 14, wherein the PEEP valve comprises:
- a regulator outlet;
- a reservoir coupled to the regulator outlet, the reservoir having at least one opening extending therethrough; and
- a reservoir outlet adapted to be coupled to suction tubing.

20. The nasal interface device according to claim 14, further comprising a pressure measuring connection extending through the body and in fluid communication with the hollowed cavity.

* * * * *